United States Patent
Wellisz

[11] Patent Number: 5,743,913
[45] Date of Patent: Apr. 28, 1998

[54] READILY EXPANSIBLE BONE FIXATION PLATE

[76] Inventor: Tadeusz Z. Wellisz, 536 S. Rimpau Blvd., Los Angeles, Calif. 90020

[21] Appl. No.: 831,907

[22] Filed: Apr. 2, 1997

[51] Int. Cl.⁶ ............................................. A61B 17/80
[52] U.S. Cl. ............................................. 606/69; 606/72
[58] Field of Search .................... 606/69, 70, 71, 606/72, 73, 60, 61

[56] References Cited

U.S. PATENT DOCUMENTS

| | | |
|---|---|---|
| 4,587,963 | 5/1986 | Leibinger et al. |
| 4,763,548 | 8/1988 | Leibinger et al. |
| 5,139,497 | 8/1992 | Tilghman et al. ............ 606/69 |
| 5,201,737 | 4/1993 | Leibinger et al. |
| 5,263,980 | 11/1993 | Leibinger et al. |
| 5,468,242 | 11/1995 | Reisberg ........................ 606/69 |
| 5,578,036 | 11/1996 | Stone et al. ................... 606/69 |

FOREIGN PATENT DOCUMENTS 4028021  5/1991  Germany.

*Primary Examiner*—Guy V. Tucker
*Attorney, Agent, or Firm*—William W. Haefliger

[57] ABSTRACT

A surgical connector that comprises a grid plate having multiple openings therethrough; the plate having multiple nodes distributed over the plate area; the plate defining multiple curved ribs interconnecting the nodes; there being at least three curved ribs connected to each node; the openings defined between the ribs.

11 Claims, 2 Drawing Sheets

READILY EXPANSIBLE BONE FIXATION PLATE

BACKGROUND OF THE INVENTION

This invention relates generally to fixation plates used for fixation of bone tissue, for example to stabilize fractures, and more particularly, to improvements in such plates having grid configuration facilitating use of such plates.

Bone fixation plates and fasteners are used to align and stabilize fractures of bony tissue, while normal tissue healing occurs. Bone plate and fastener fixation systems are intended for use in the treatment of fractures, osteotomy procedures, and reconstructive procedures. Fixation systems include a variety of plate configurations for different anatomical applications. Screws or other fasteners are included for fixation of the plates to the bony tissue.

Traditional bone plates are linear constructs that contain holes to accept fasteners that attach the plate to the underlying bone. Many plates are designed to be malleable to allow them to be contoured by the end user to adapt to the contour of the bone.

Sheets, grids, screens, and mesh plates can also be used to stabilize bony tissue. They can also span gaps in bony tissue and can serve to provide structural support, restore the contour of the tissue and act as a barrier between tissue planes. They can be contoured by bending, folding, or rolling. Rolling can be useful when a mesh plate is to be adapted to a tubular structure, such as a long bone.

The ability to adapt sheets, grids, screens, and mesh plates to complex three-dimensional shapes, such as those present in the craniofacial skeleton, is limited. This is because, although sheets, grids, screens, and mesh plates are malleable, they are not designed to stretch, and the distances between any two points on the grid or plate surface remain essentially unchanged as bending, folding, or rolling takes place. An analogy is the ability to wrap a piece of paper around a spherical object, such as a ball: doing so will result in pleats and folds in the paper. If such a pleat or fold were to occur in a sheet, grid, screen, or mesh plate used to stabilize bony tissue, both a weakening of the fixation and a contour deformity could occur.

There is great need for fixation plates configured to overcome problems and difficulties in their use, for example as referred to above.

SUMMARY OF THE INVENTION

It is a major object of the invention to provide an improved device used to stabilize, fixate or align bony or cartilaginous tissue. As will be seen, the device is made of a malleable, implantable material, such as a biocompatible metal or polymer. The device, partially or in its entirety, has the shape of a lattice with curved members, such as arms or ribs that intersect. The distances between the points of intersection of some or all of the arms, can be varied to allow the device to be shaped to fit a precise three-dimensional contour, or the contour of bony or cartilaginous tissue.

The distance between the nodes of the mesh can be varied for precise matching to three-dimensional alignment of the bony tissue. The fact that the arms connecting the nodes in the mesh are curved allows the distances between the individual nodes to be changed, thus allowing for contouring in three dimensions.

Accordingly, it is a further object to provide a connector device as referred to, and characterized by, provision of:

a) a grid plate having multiple openings therethrough, b) the plate having multiple nodes distributed over the plate area, c) the plate defining multiple curved arms or ribs interconnecting the nodes, d) there being at least three curved ribs connected to each node, e) the openings defined between the ribs.

As will appear, there are typically four of the curved ribs or arms connected to each node; and each curved rib has arched configuration in the plane of the plate.

Another object is to provide the openings through the plate to have elongated dumb bell configuration, with narrow, intermediate zones and enlarged end zones.

Yet another object is to provide the plate with elongated tabs located at different sides of the plate, each tab connected to multiple of said ribs. There are typically three of such tabs located at three sides of the plate.

A further object is to provide multiple rows of holes located in elongated anchor tabs projecting at sides of the plate, said holes adapted to receive fasteners that connect the plate to bone structure. The anchor tabs typically include a first tab extending along one side of the plate and integral with certain of said nodes, and second tabs that project from the first tab, and away from the plate.

An additional object is to provide a plate as described which is deformed to have compound curvature defining a dome. The plate may be deformed in an X, Y, Z rectangular coordinate system, the plate having curvature in X-Z planes, and the plate having curvature in Y-Z planes.

These and other objects and advantages of the invention, as well as the details of an illustrative embodiment, will be more fully understood from the following specification and drawings, in which:

DRAWING DESCRIPTION

DETAILED DESCRIPTION

Figure 1:
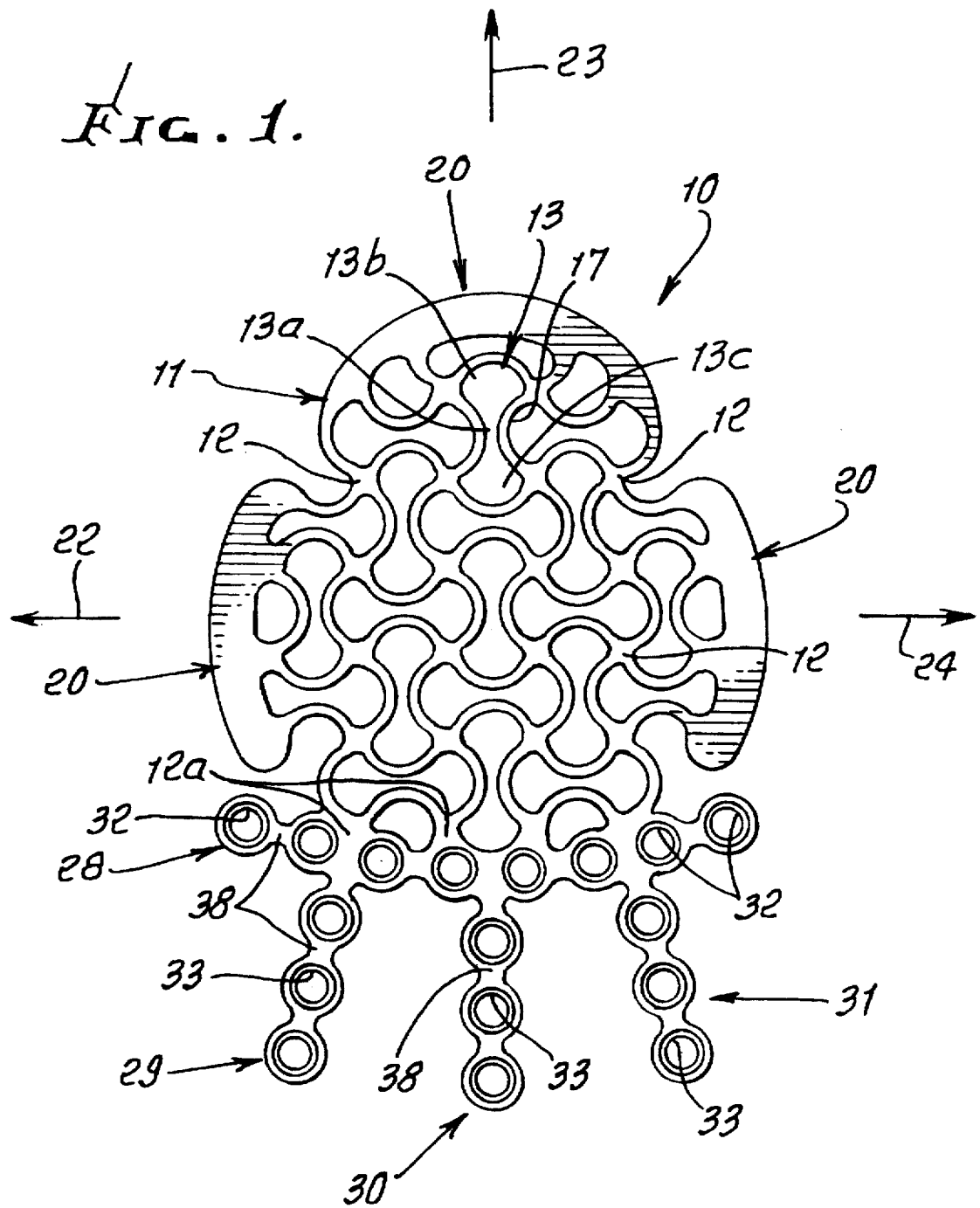
FIG. 1 is a plan view of a connector grid plate incorporating the invention.

Referring to FIG. 1, a surgical connector 10, of preferred form, includes a grid plate 11 having multiple, like, small nodes 12 distributed over the plate area. There are also like, dumbbell-shaped, elongated openings 13 extending through the plate structure, each such opening including a reduced width central zone 13a, and two enlarged end openings 13b and 13c interconnected by 13a.

Figure 2:
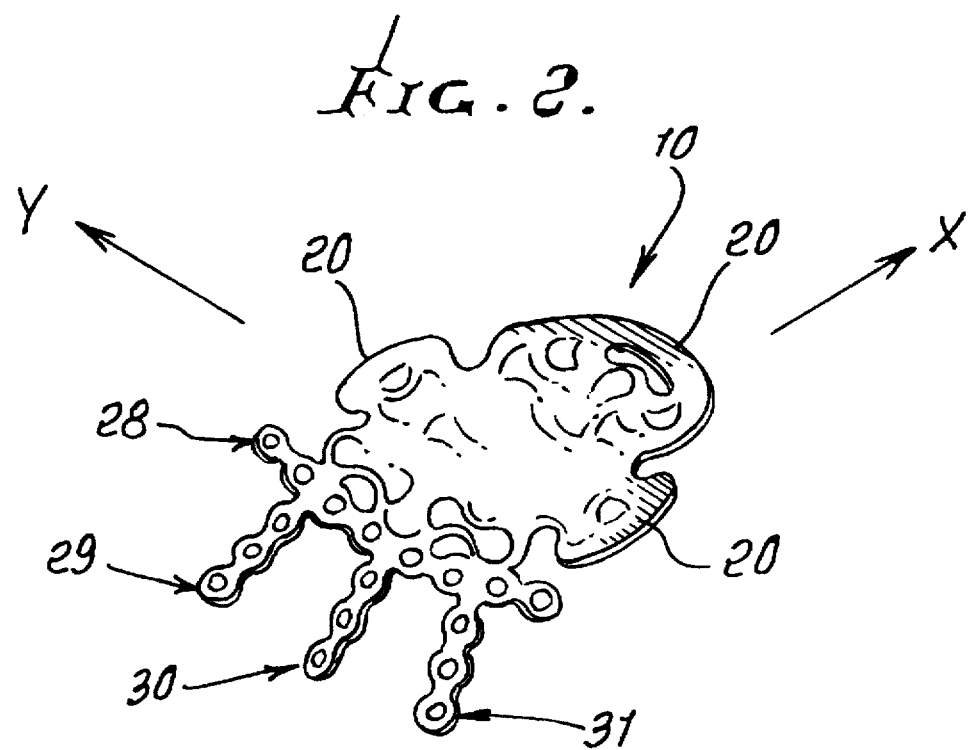
FIG. 2 is a perspective view of the FIG. 1 plate, deformed to have compound curvature.

The plate also has multiple, curved, narrow ribs 17, each rib extending between two of the nodes, and there being four of the ribs joined to each node at 90°, 180°, 270°, and 360° locations about the node. The openings 13 are defined by and between the ribs 17, as shown. Note that each rib has arch shape in the plane of the plate. This rib and node construction allows or facilitates manual deformation of the plate to have dome shape, i.e., compound curvature, as in X-Z and Y-Z planes in an X, Y, Z rectangular coordinate system seen in FIG. 2. The plate may consist of bendable material, which takes a permanent set, as the plate is deformed.

The plate also forms elongated tabs located at different sides of the plate, each tab connected to multiple ribs. See the three like tabs 20 located at three sides of the plate (12 o'clock, 3 o'clock and 9 o'clock). Such tabs may be finger gripped and manipulated (pushed, pulled) to deform the plate to desired shape; see for example expansion in the direction of arrows 22–24; and deformation to FIG. 2 dome shape, which also may be expanded. Such expansion may be locally controlled to shape the plate to existing irregular bone structure, as on the human skull.

The plate also includes multiple rows of holes located in and along elongated anchor tabs projecting at a side of the plate. Such holes are adapted to receive fasteners that connect the plate to bone structure. See FIG. 3.

The anchor tabs typically include a first tab 28 extending along one side of the plate, as at 6 o'clock position, and integral with certain 12a of the nodes; and second tabs 29, 30 and 31 that project linearly from locations along the first tab and away from the plate. Note the eight fastener holes 32 in curved tab 28, and fastener holes 33 in the tabs 29, 30 and 31. Tabs 28, 29, 30, and 31, which have chain-like configuration, may be considered as anchor tabs and are easily bendable to conform to bone structure. Note narrowed, bendable regions 38 between holes.

Figure 3:
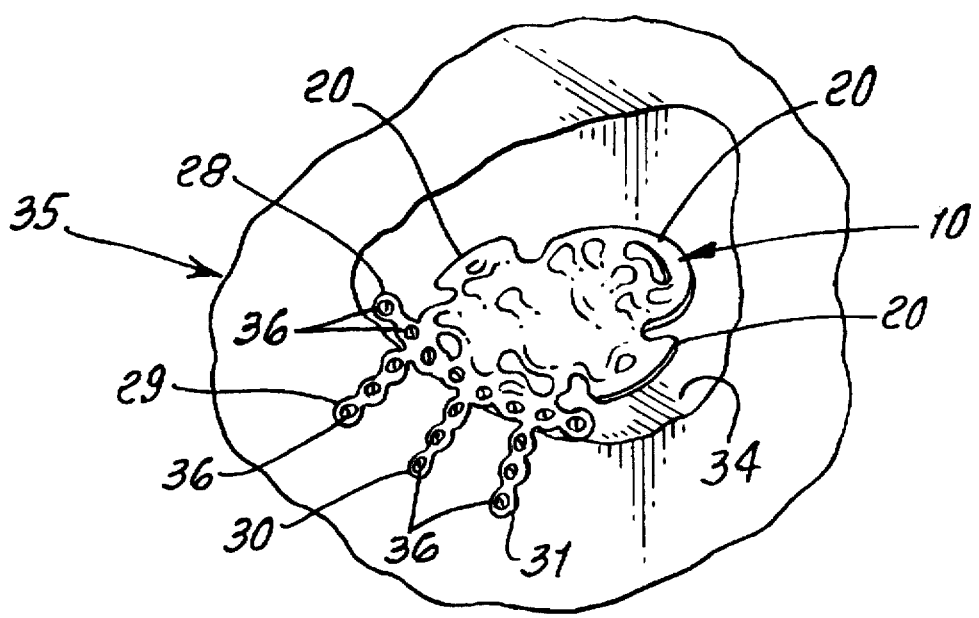
FIG. 3 is a view showing use of the FIG. 1 plate.

In FIG. 3, the connector 10 is conformed to the recessed orbital lower wall 34 of a human skull 35, and to which the plate is fitted by manual deformation. Fastener screws 36 attach the curved tab 28 to the curved outer rim of the wall 34; and similar screws attach the elongated anchor tabs 29–31 to the outer surface of the skull bone.

A preferred plate, as described, consists of titanium, although stainless steel synthetic polymers (such as polyethylene or polypropylene) are usable. Poly-lactic and polygelactic materials are also usable.

Between 0.2 and 0.5 of the plate overall area is solid material, allowing plate stretachability or expansion in three directions (X, Y, and Z directions in a rectangular coordinate system). Hole 32 and 33 diameters are between 0.067 and 0.035 inches; outer diameter of the rings 16 are between 0.125 and 0.160 inches; and the radii of the circularly curved ribs 17 are between 0.08 and 0.04 inches. Curved tab 28 has a radius between 1.0 and 2.5 inches. Tabs 29, 30, and 31 project generally radially from the plate and at angles between 5° and 35° from one another. Plate thickness is between 0.012 and 0.025 inches and is generally uniform.

The plate material may be biamenar, or multiamenar; or the plate material may be a composite, such as titanium base, onto which is deposited a polymer or protein layer. The second or outer layer may act as a lattice to promote tissue ingrowth and thus healing. An example is a second or outer layer consisting of polyethylene granules. In this regard, healing of bone is frequently delayed or incomplete. It is known that certain substances, generally referred to as growth factors, can increase the rate and/or the amount of bone healing. One issue pertaining to the use of growth factors is that they are rapidly cleared from the body by the body's circulatory system. The ability to bind the growth factors to a polymer or protein layer may have the effect of localizing and prolonging the activity of the growth factors. The defect would require structural support until such time that the defect was to heal.

I claim:

1. A surgical connector comprising:

a) grid plate having multiple openings therethrough, b) said plate having multiple nodes distributed over the plate area, c) the plate defining multiple curved ribs interconnecting said nodes, d) there being at least three curved ribs connected to each node, e) said openings defined between said ribs, said openings having elongate dumb bell configuration, with narrow intermediate zones and enlarged end zones, f) the plate forming elongated tabs located at different sides of the plate, each tab connected to multiple of said ribs, each tab having length exceeding the length of each said elongate dumb bell configuration, each tab having width throughout its length exceeding the widths of the ribs to which it is connected.

2. The connector of claim 1 wherein there are four of said curved ribs connected to each node.

3. The connector of claim 1 wherein each curved rib has arch configuration.

4. The connector of claim 1 wherein there are three of said tabs located at three sides of the plate.

5. The connector of claim 1 wherein the plate includes multiple rows of holes located in elongated anchor tabs projecting at sides of the plate, said holes adapted to receive fasteners that connect the plate to bone structure.

6. The connector of claim 5 wherein said anchor tabs include a first tab extending along one side of the plate and integral with certain of said nodes, and second tabs that project from said first tab, and away from the plate.

7. The connector of claim 5 including fasteners passing through said holes.

8. The connector of claim 5 wherein said second tabs project relatively divergently.

9. The connector of claim 1 wherein the plate is deformed to have compound curvature defining a dome.

10. The connector of claim 1 wherein the plate is deformed in an X, Y, Z rectangular coordinate system, the plate having curvature in X–Z planes, and the plate having curvature in Y–Z planes.

11. The connector of claim 1 wherein the plate has uniform thickness.

* * * * *